United States Patent
Hwang et al.

(10) Patent No.: US 7,495,126 B2
(45) Date of Patent: Feb. 24, 2009

(54) PROCESS OF PREPARATION OF SUBSTITUTED TETRAFLUOROBENZYLANILINE COMPOUND AND ITS PHARMACEUTICALLY APPROVED SALTS

(75) Inventors: Tae-Seop Hwang, Suwon-si (KR); Hyun-Gyu Kim, Gwangmyeong-si (KR)

(73) Assignee: Choongwae Pharma Corporation, Seoul (KR)

( * ) Notice: Subject to any disclaimer, the term of this patent is extended or adjusted under 35 U.S.C. 154(b) by 0 days.

(21) Appl. No.: 11/915,180

(22) PCT Filed: May 25, 2006

(86) PCT No.: PCT/KR2006/001993

§ 371 (c)(1),
(2), (4) Date: Nov. 21, 2007

(87) PCT Pub. No.: WO2006/126846

PCT Pub. Date: Nov. 30, 2006

(65) Prior Publication Data

US 2008/0167492 A1  Jul. 10, 2008

(30) Foreign Application Priority Data

May 25, 2005  (KR) ............... 10-2005-0044298

(51) Int. Cl.
  *C07C 229/00*  (2006.01)
  *C07C 249/00*  (2006.01)
(52) U.S. Cl. .................. 562/456; 562/433; 562/440

(58) Field of Classification Search .............. 562/456, 562/433, 440
See application file for complete search history.

(56) References Cited

U.S. PATENT DOCUMENTS

| 5,527,814 A | 6/1996 | Louvel |
| 6,927,303 B2 * | 8/2005 | Gwag et al. ............. 560/136 |

FOREIGN PATENT DOCUMENTS

| JP | 2000-212141 A | 8/2000 |
| JP | 2000-273041 A | 10/2000 |
| KR | 10-2003-0097706 A | 12/2003 |
| KR | 10-2004-0066639 A | 7/2004 |
| WO | WO 99/01421 A | 1/1999 |
| WO | WO 2004/000786 A1 | 12/2003 |

OTHER PUBLICATIONS

Derdau, V., et al., "Condensation of Laterally Lithiated o-Methyl and o-Ethyl Benzamides with Imines Mediated by (−) Sparteine, Enantioselective Synthesis of Tetrahydroisoquinolin-1-ones," J. Org. Chem. 2001, 66, 1992-1998.

Andrews, Philip, C., et al., "Gallium metal mediated allylation of carbonyl compounds and imines under solvent-free conditions," Tetrahedron Letters, 45 (2004) 243-248.

* cited by examiner

*Primary Examiner*—Karl J Puttlitz
(74) *Attorney, Agent, or Firm*—Sughrue Mion, PLLC

(57) ABSTRACT

This invention relates to a method for preparing tetrafluorobenzyl-5-aminosalicylic acid derivative and its pharmaceutically acceptable salt compounds. In particular, this invention relates to a method for preparing tetrafluorobenzyl-5-aminosalicylic acid derivative and its pharmaceutically acceptable salts by using tetrafluorobenzilidine-5-aminosalicylic acid derivative as an intermediate.

3 Claims, 1 Drawing Sheet

Quantification of Infarct Volume

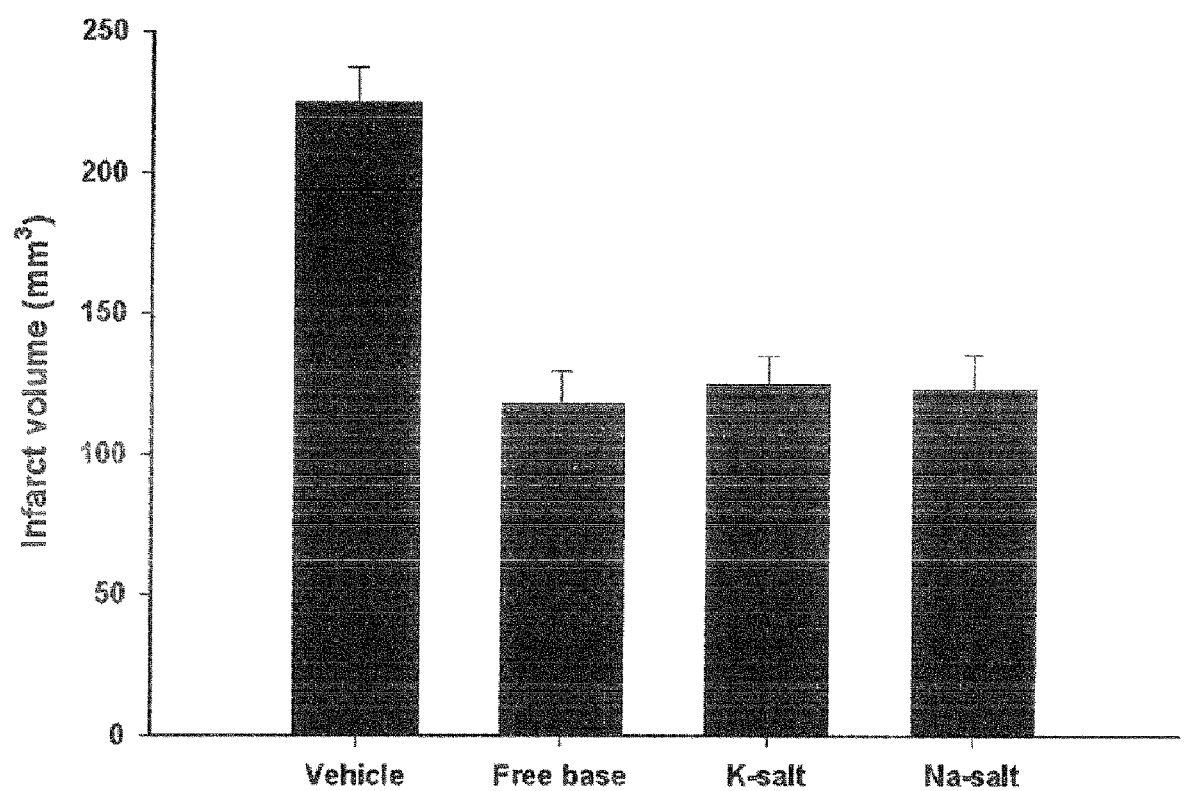
[Fig. 1]
Quantification of Infarct Volume

PROCESS OF PREPARATION OF SUBSTITUTED TETRAFLUOROBENZYLANILINE COMPOUND AND ITS PHARMACEUTICALLY APPROVED SALTS

TECHNICAL FIELD

This invention relates to a process for preparing tetrafluorobenzyl-5-aminosalicylic acid derivatives represented by the following Chemical Formula I and its pharmaceutically acceptable salt compounds which are useful for the prevention and treatment of acute and chronic neurodegenerative diseases.

<Chemical formula I>

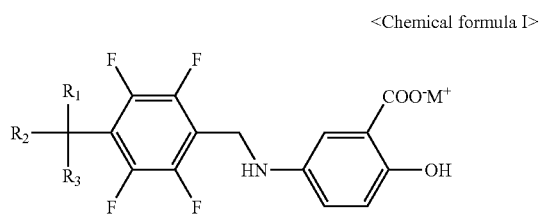

Wherein, $M^+$ represents lithium, sodium or potassium; and $R_1$, $R_2$ and $R_3$ may, independently of one another, be hydrogen or halogen.

BACKGROUND ART

The Korean Patent Unexamined Publication Nos. 2003-0097706 and 2004-0066639 disclose that tetrafluorobenzyl derivatives are therapeutically effective in the prevention and treatment of acute and chronic neurodegenerative diseases and can effectively be used to prevent and treat chronic neurodegenerative diseases such as Alzheimer's disease, Parkinson's disease and Huntington's disease; seizure-inducing brain disease such as epilepsy; and ischemic brain disease such as stroke.

The process for preparing tetrafluorobenzyl-5-aminosalicylic acid derivatives is described in the Korean Patent Unexamined Patent No. 2003-0097706, and is illustrated in the following reaction scheme II.

<Reaction scheme II>

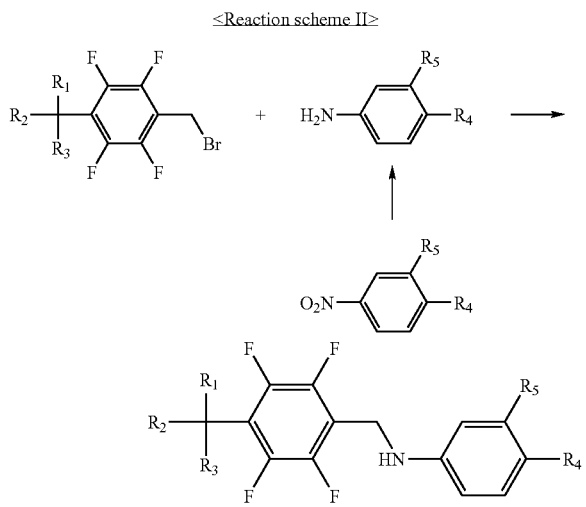

Wherein, $R_1$, $R_2$ and $R_3$ are hydrogen or halogen, respectively; $R_4$ is hydroxy, alkyl, alkoxy, halogen, alkoxy substituted with halogen, alkanoyloxy or nitro, and $R_5$ is carboxylic acid or ester of carboxylic acid substituted with C1-C4 alkyl, carboxyamide, sulfonic acid, halogen or nitro.

Reaction scheme II shows the process for preparing tetrafluorobenzyl-5-aminosalicylic acid derivatives. First, a nitrobenzene compound is hydrogenated, and the resulting aniline compound is reacted with tetrafluorobenzyl bromide compound in the presence of triethylamine and dimethylformimide resulting in the production of the desired tetrafluorobenzyl-5-aminosalicylic acid derivative.

The process, however, also results in the formation of a dimer (Chemical Formula III) in quantities greater than 1% of the total product. The dimmer is formed as a result of the side-reaction between the starting material, tetrafluorobenzyl bromide compound, and the secondary amine group of a tetrafluorobenzyl-5-aminosalicylic acid derivative. The dimer is not easily removed by general re-crystallization methods, and a more complex purification process is required in order to stay under the impurity guideline of 0.1%. This reaction scheme is therefore inadequate for industrial application. It produces a reduced yield of the desired compound, and thereby increases manufacturing costs.

<Chemical formula III>

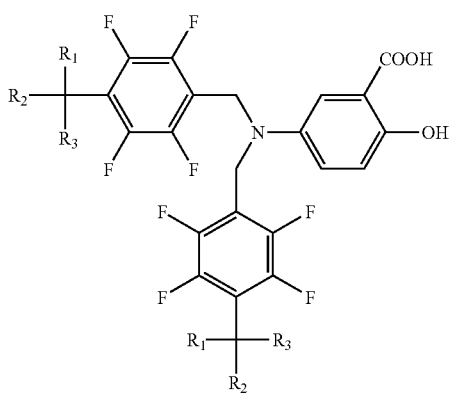

Wherein, $R_1$, $R_2$ and $R_3$ may, independently of one another, be hydrogen or halogen.

Furthermore, the Korean Patent Unexamined Patent No. 2003-0097706 fails to describe the salt compounds of tetrafluorobenzyl-5-aminosalicylic acid derivative in more detail. Thus, another formulation research of the aforementioned compound in terms of stability is required.

Through intensive and thorough research, the inventors have found that dimer formation in the manufacturing of tetrafluorobenzyl-5-aminosalicylic acid derivative may be avoided by using a tetrafluorobenzilidine-5-aminosalicylic acid derivative as an intermediate. As well, the stability of the desired compound was improved by preparing the salt compound using alkali metals, thus leading to this invention.

DISCLOSURE OF INVENTION

Technical Problem

An object of this invention is to provide a novel method for producing tetrafluorobenzyl-5-aminosalicylic acid derivatives while preventing the formation of impurities such as the dimer represented by Chemical Formula III.

In particular, another object of this invention is to provide a novel method for producing tetrafluorobenzyl-5-aminosalicylic acid derivatives by using a tetrafluorobenzilidine-5-aminosalicylic acid derivative represented by Chemical Formula II as an intermediate.

Further, another object of this invention is to provide the salt compounds of tetrafluorobenzyl-5-aminosalicylic acid derivatives which have increased stability and less toxicity.

Technical Solution

The novel method for producing tetrafluorobenzyl-5-aminosalicylic acid is shown in reaction scheme I. The preparation is comprised of the following steps:

a) oxidation of tetrafluorobenzyl alcohol, represented by Chemical Formula 1 to tetrafluorobenzaldehyde represented by Chemical Formula 2;

b) conversion of tetrafluorobenzaldehyde to tetrafluorobenzilidine-5-aminosalicylic acid derivative represented by Chemical Formula II via dehydration-condensation reaction between tetrafluorobenzaldehyde and 5-amino-salicylic acid represented by Chemical Formula 3, and c) hydrogenation of tetrafluorobenzilidine-5-aminosalicylic acid derivative to tetrafluorobenzyl-5-aminosalicylic acid represented by Chemical Formula I.

<Reaction scheme I>

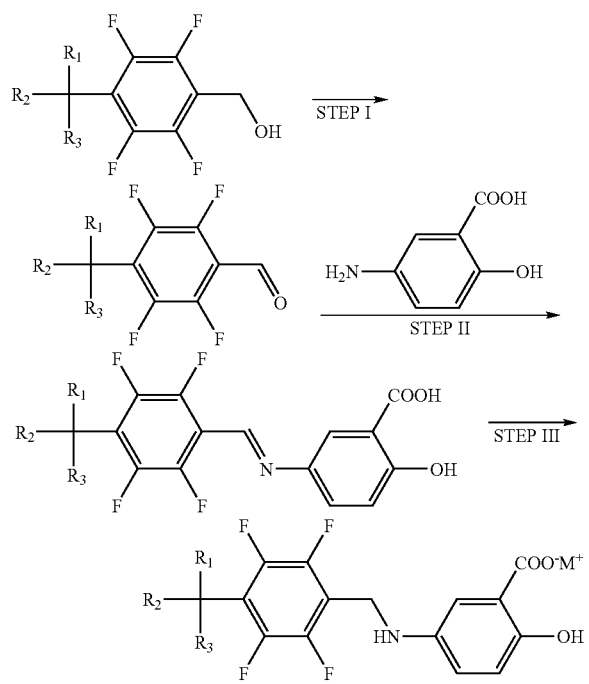

Wherein, $M^+$ represents lithium, sodium or potassium; and $R_1$, $R_2$ and $R_3$ may, independently of one another, be hydrogen or halogen.

<Chemical formula I>

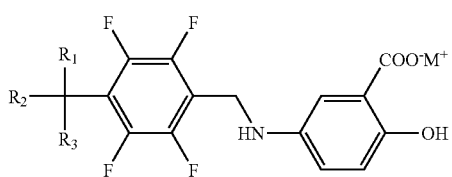

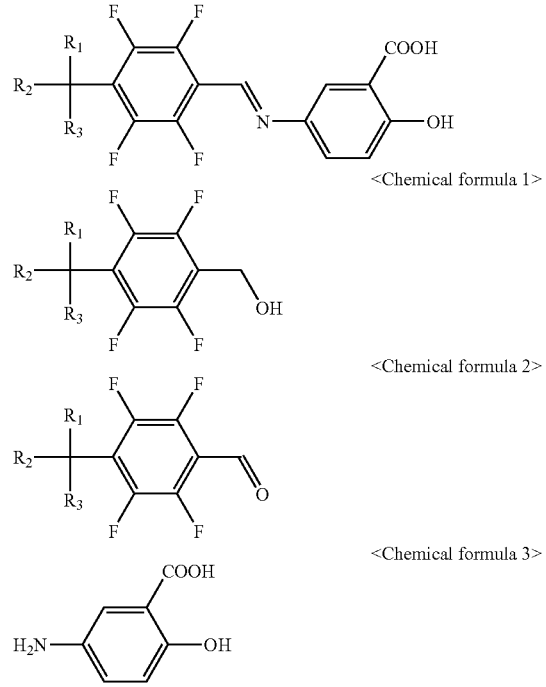

<Chemical formula II>

<Chemical formula 1>

<Chemical formula 2>

<Chemical formula 3>

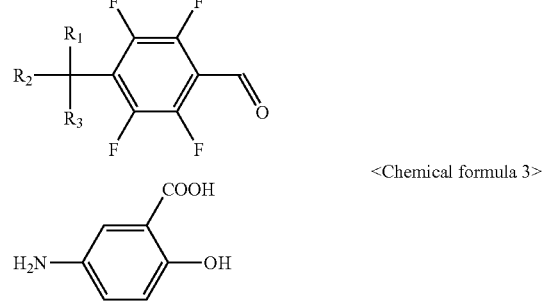

Wherein, $M^+$ represents lithium, sodium or potassium; and $R_1$, $R_2$ and $R_3$ may, independently of one another, be hydrogen or halogen.

In a further aspect of this invention 2-hydroxy-5-[(2,3,5,6-tetrafluoro-4-trifluoromethyl-benzilidine)-amino]benzoic acid, represented by Chemical Formula II, is provided as a novel intermediate compound for producing tetrafluorobenzyl-5-aminosalicylic acid compound, represented by Chemical Formula I.

The tetrafluorobenzyl-5-aminosalicylic acid compound of this invention is synthesized by the reaction scheme I as follows:

1) Step I: Tetrafluorobenzaldehyde is formed via oxidation of tetrafluorobenzyl alcohol;

2) Step II: Tetrafluorobenzaldehyde, as obtained in step I, and 5-amino-salicylic acid undergo a dehydration-condensation reaction in the presence of methylene chloride solvent at room temperature using molecular sieves to form tetrafluorobenzilidine-5-aminosalicylic acid derivative, represented by Chemical Formula II, as an imine compound; and 3) Step III: The tetrafluorobenzilidine-5-aminosalicylic acid derivative obtained in step II and represented by Chemical Formula II is hydrogenated using a platinum catalyst and alcohol solvent to produce tetrafluorobenzyl-5-aminosalicylic acid compounds, represented by Chemical Formula I, via contact reduction.

The above processes are explained in more detail as set forth hereunder.

Tetrafluorobenzaldehyde in step I may be easily prepared via general oxidation of tetrafluorobenzyl alcohol using pyridinium chlorochromate and methylene chloride.

In step II, tetrafluorobenzaldehyde, as obtained in step I, and 5-amino-salicylic acid undergo a dehydration-condensation reaction at room temperature to form tetrafluorobenzilidine-5-aminosalicylic acid derivative, represented by Chemical Formula II, according to the procedures reported in J. Org. Chem., 66(6), 2001, 1992~1998.

Weak acidic reagents (such as paratoluene sulfonic acid) may be used in the dehydration-condensation reaction; as reported in Tetrahedron Lett., 45(2), 2003, 243~248. The obtained compound is re-crystallized from alcohol or diethylether to obtain a higher quality compound, represented by Chemical Formula II. The processes of this invention are economically feasible in that the desired compound can be prepared using continuous processes without a separate purification process.

Therefore, step II of this invention is characterized by avoiding a dimer generated in the process of preparing tetrafluorobenzyl-5-aminosalicylic acid compound of the Chemical Formula I, which is reported by the Korean Patent Unexamined Publication No. 2003-0097706.

In step III, a tetrafluorobenzilidine-5-aminosalicylic acid derivative represented by Chemical Formula II, as obtained in step II, is hydrogenated using a palladium catalyst and alcohol solvent to produce a tetrafluorobenzyl-5-aminosalicylic acid compound, represented by Chemical Formula I, via contact reduction.

The reduction reaction of the imine compound in step III of this invention can be performed to give the desired compound, represented by Chemical Formula I, via other general and common reduction procedures using sodium borohydride and alcohol; or a transition metal catalyst and weak acid such as acetic acid.

This invention provides a novel method for producing tetrafluorobenzyl-5-aminosalicylic acid derivative to prevent the formation of impurities such as the dimer represented by Chemical Formula III.

Of particular mention is that this invention is characterized by using a tetrafluorobenzilidine-5-aminosalicylic acid derivative (Chemical Formula II) as an intermediate in order to prevent the formation of a dimer.

A further aspect of this invention provides the pharmaceutically acceptable salts of tetrafluorobenzyl-5-aminosalicylic acid, represented by Chemical Formula I. The pharmaceutically acceptable salts of the desired compound in this invention include alkali metals such as sodium, potassium and lithium.

The salts of the desired compound represented by Chemical Formula I of this invention can be prepared by direct crystallization or by lyophilization using an inorganic reagent such as lithium hydroxide, sodium hydroxide or potassium hydroxide in the presence of alcohol, acetone, acetonitrile and other organic solvents.

The pharmaceutically acceptable salts in this invention were selected according to the following criteria.

The inventors have screened various kinds of the pharmaceutically acceptable salts of the desired compound represented by Chemical Formula I such as alkali metals; alkaline earth metals such as calcium; pharmaceutically acceptable nontoxic salts such as hydrochloric acid, phosphoric acid, sulfuric acid, nitric acid, maleic acid, acetic acid, or citric acid; and organic salts such as N,N-dibenzylethylene diamine or ethylene diamine.

The acid addition compounds and their salts such as sodium, potassium, and lithium, as prepared in Examples 3-6, were stirred in a water bath shaker at 25° C., 100 rpm for 48 hours to measure their solubility in water. It was observed that acid (free base) compounds are poorly soluble in water, whereas sodium, potassium and lithium salts had solubilities of 25~80 mg/ml, 590 mg/ml and 500 mg/ml, respectively, depending on the crystallization method.

When using nontoxic acids combined at the amine, reactions were not observed; and the desired product was not formed. In experiments using organic salts, a reaction was observed and the desired product obtained; but they were poorly soluble in water.

Therefore the processes to produce the desired compound using various acids or organic salts were excluded from this invention. The pharmaceutically acceptable salts of the desired compound which include alkaline earth metals such as calcium were also excluded due to their poor solubility in water.

Therefore this invention provides the salts of sodium, potassium and lithium to have better solubility and stability among the pharmaceutically acceptable salts of the desired compound represented by the chemical formula I.

These salts of this invention have better stability profile in oral dosage form with less toxicity.

Advantageous Effects

As aforementioned, this invention provides a novel method for producing tetrafluorobenzyl-5-aminosalicylic acid derivative; a method which prevents the formation of impurities such as the dimer represented by Chemical Formula III.

This invention provides a novel method for producing tetrafluorobenzyl-5-aminosalicylic acid derivative by using tetrafluorobenzilidine-5-aminosalicylic acid derivative, represented by Chemical Formula II, as an intermediate.

Another object of this invention is to provide the salt compounds of tetrafluorobenzyl-5-aminosalicylic acid derivative with better stability of the desired compound and with less toxicity.

BRIEF DESCRIPTION OF THE DRAWINGS

FIG. 1 shows the protective effects of the tetrafluorobenzyl-5-aminosalicylic acid compound, as well as the protective effects of the potassium and sodium salt forms of tetrafluorobenzyl-5-aminosalicylic acid in rats with focal cerebral ischemia by occlusion of the middle cerebral artery.

BEST MODE FOR CARRYING OUT THE INVENTION

This invention will now be described in reference to the following examples and experimental examples, which are merely illustrative and are not to be construed as a limitation of the scope of this invention.

EXAMPLE 1

Preparation of 2,3,5,6-tetrafluoro-4-trifluoromethyl-benzaldehyde 2,3,5,6-tetrafluorobenzyl alcohol (49.62 g, 0.200 mole) and methylene chloride (500 ml) are stirred at room temperature for complete dissolution and then pyridinium chlorochromate (73.29 g, 0.340 mole) was slowly added to the reaction mixture. The reaction mixture was refluxed for 4 hours while the reaction temperature was allowed to increase; and then cooled. After the undissolved material was filtered under reduced pressure, the residue was washed with 500 ml purified water and 500 ml saturated physiological saline. The separated oil layer was dried over $MgSO_4$ (5 g) and concentrated under reduced pressure to give the desired compound; 48.23 g of 2,3,5,6-tetrafluorobenzaldehyde (0.196 mole, 98.0% yield) as a yellow oil.

$^1$H NMR($CDCl_3$, 300 MHz): 10.35(m, 1H)

EXAMPLE 2

Preparation of 2-hydroxy-5-[(2,3,5,6-tetrafluoro-4-trifluoromethyl-benzilidine)-amino]benzoic acid 5-amino-salicylic acid (33.02 g, 0.216 mole) was added to a solution of 2,3,5,6-tetrafluorobenzaldehyde (48.23 g, 0.196 mole), as prepared in Example 1, and methylene chloride (500 ml). The reaction mixture was stirred for 10 minutes and after the addition of 4 Å molecular sieves (5.0 g); stirred at room temperature for 16 hours. After the undissolved material was filtered under reduced pressure, the residue was washed with 500 ml purified water and 500 ml saturated physiological saline. The separated oil layer was dried over $MgSO_4$ (5 g) and filtered under reduced pressure. The oil solution was concentrated under reduced pressure to obtain 2-hydroxy-5-[(2,3,5,6-tetrafluoro-4-trifluoromethyl-benzilidine)-amino]benzoic acid as a yellow oil solution. The residue was re-crystallized from ethanol (200 ml) and dried under reduced pressure to give 65.97 g (0.173 mole, 88.3% yield) of the desired white solid.

$^1$H NMR($CDCl_3$, 300 MHz): 7.12(dd, 1H), 7.57(d, 1H), 7.95(d, 1H), 8.39(s, 2H)

EXAMPLE 3

Preparation of 2-hydroxy-5-(2,3,5,6-tetrafluoro-4-trifluoromethyl-benzylamino)benzoic acid 5-amino-salicylic acid (33.02 g, 0.216 mole) was added to a solution of 2,3,5,6-tetrafluorobenzaldehyde (48.23 g, 0.196 mole), as prepared in Example 1, and methylene chloride (500 ml). The reaction mixture was stirred for 10 minutes and after the addition of 4 Å molecular sieves (5.0 g), stirred at room temperature for 16 hours. The undissolved material was filtered under reduced pressure and dried over $MgSO_4$ (10 g). The solution was concentrated under reduced pressure and then ethanol (600 ml) was added to the residue. A platinum catalyst (9.65 mg) was added to the solution and stirred at 20-25° C. for 2 hours under 4 atm. The undissolved material was filtered under reduced pressure and concentrated to remove the solvent. Ethylacetate (500 ml) and purified water (500 ml) was added to the conc. residue. The solution was cooled to 5-10° C. and then the pH of the solution was adjusted to 1.0-1.5 using hydrochloric acid; while keeping the temperature steady at 5-10° C. The solution was stirred for 30 minutes at room temperature and left alone. The separated oil layer was washed with 500 ml purified water and 500 ml saturated physiological saline in due order. Active charcoal (5 g) was added to the separated oil layer and stirred for 1 hour at room temperature. The oil layer was filtered under reduced pressure and concentrated to obtain the residue as a pale white solid. Ethylacetate (100 ml) was added to the conc. residue and the temperature was allowed to rise to 50° C. for complete dissolution. n-hexane (400 ml) was added to the reaction mixture and then the solution was cooled to 5-10° C. and stirred for 6 hours. The precipitated crystals were filtered and dried under reduced pressure to give 63.99 g (0.167 mole, 85.2% yield) of 2-hydroxy-5-(2,3,5,6-tetrafluoro-4-trifluoromethyl-benzylamino)benzoic acid as the desired compound. (HPLC purity: more than 99.8%)

$^1$H NMR($CDCl_3$, 300 MHz): 4.41(s, 2H), 6.77(d, 1H), 6.94(dd, 1H), 7.08(d, 1H)

EXAMPLE 4

Preparation of potassium 2-hydroxy-5-(2,3,5,6-tetrafluoro-4-trifluoromethyl-benzylamino)benzoate <Method 4-1>

2-hydroxy-5-(2,3,5,6-tetrafluoro-4-trifluoromethyl-benzylamino)benzoic acid (10 g, 0.261 mole), as prepared in Example 3, was added to anhydrous ethanol (500 ml) and then the temperature was allowed to rise to 50° C. for complete dissolution. The resulting solution was cooled to 10° C. The pH of the solution was adjusted to 6.8-7.0 using a separately prepared solution of 85%-potassium hydroxide (17.22 g, 0.261 mole) and anhydrous ethanol (30 ml). The reaction mixture was stirred for 2 hours at room temperature and then the precipitated crystals were filtered and dried to give 100.8 g (0.239 mole, 91.7% yield) of potassium 2-hydroxy-5-(2,3,5,6-tetrafluoro-4-trifluoromethyl-benzylamino)benzoate as the desired compound.

<Method 4-2>

2-hydroxy-5-(2,3,5,6-tetrafluoro-4-trifluoromethyl-benzylamino)benzoic acid (10 g, 0.261 mole), as prepared in Example 3, was added to purified water (3000 ml) and then the resulting solution was cooled to 10° C. At the same temperature, the pH of the solution was adjusted to 6.8-7.0 using 1N-potassium hydroxide solution and stirred for another 2 hours. The solution was lyophilized to give 109.9 g (0.261 mole, 100.0% yield) of potassium 2-hydroxy-5-(2,3,5,6-tetrafluoro-4-trifluoromethyl-benzylamino)benzoate as the desired compound.

EXAMPLE 5

Preparation of sodium 2-hydroxy-5-(2,3,5,6-tetrafluoro-4-trifluoromethyl-benzylamino)benzoate <Method 5-1>

Repeating the procedure in Method 4-1 of Example 4; except replacing potassium hydroxide with the same number of moles of sodium hydroxide; 96.75 g (0.239 mole, 91.5% yield) of sodium 2-hydroxy-5-(2,3,5,6-tetrafluoro-4-trifluoromethyl-benzylamino)benzoate was obtained as the desired compound.

<Method 5-2>

Repeating the procedure in Method 4-2 of Example 4; except replacing potassium hydroxide with the same number of moles of sodium-2-ethylhexanoate; 97.70 g (0.241 mole, 92.4% yield) of sodium 2-hydroxy-5-(2,3,5,6-tetrafluoro-4-trifluoromethyl-benzylamino)benzoate was obtained as the desired compound.

<Method 5-3>

Repeating the procedure in Method 4-2 of Example 4; except replacing potassium hydroxide with the same number of moles of 1N-sodium hydroxide solution; 105.7 g (0.261 mole, 100.0% yield) of sodium 2-hydroxy-5-(2,3,5,6-tetrafluoro-4-trifluoromethyl-benzylamino)benzoate was obtained as the desired compound.

EXAMPLE 6

Preparation of lithium 2-hydroxy-5-(2,3,5,6-tetrafluoro-4-trifluoromethyl-benzylamino)benzoate <Method 1>

Repeating the procedure in Method 4-1 of Example 4; except replacing potassium hydroxide with the same number of moles of lithium hydroxide; 90.38 g (0.232 mole, 89.0% yield) of lithium 2-hydroxy-5-(2,3,5,6-tetrafluoro-4-trifluoromethyl-benzylamino)benzoate was obtained as the desired compound.

<Method 2>

Repeating the procedure in Method 4-2 of Example 4; except replacing potassium hydroxide with the same number of moles of 1N-lithium hydroxide solution; 101.5 g (0.261 mole, 100.0% yield) of lithium 2-hydroxy-5-(2,3,5,6-tetrafluoro-4-trifluoromethyl-benzylamino)benzoate was obtained as the desired compound.

EXAMPLE 7

Preparation of Injection

An injection was prepared in such a manner that each salt (Na-salt, K-salt, Li-salt), as prepared in Example 4-6, was dissolved in water for injection (WFI) at a concentration of 2 mg/ml. The solution was filled into a vial and treated in vacuo.

Experimental Example 1

Stability Test of Injectable Preparation

After each injectable was prepared as described in Example 7, they were stored at different temperatures (25° C., 40° C., 60° C.) for 6 months, the amount of active ingredients were measured using HPLC.

The following Tables 1, 2 and 3 show the residual amount of active ingredients in each injectable preparation per period.

TABLE 1

Changes in amount of sodium salt in water for injection (WFI) (mean ± standard deviation)

Sodium salt in WFI

| | Residual amount (%) | | |
|---|---|---|---|
| Time (day) | 25° C. | 40° C. | 60° C. |
| 0 | 104.15 ± 0.54 | 104.15 ± 0.54 | 104.15 ± 0.54 |
| 3 | 101.89 ± 1.16 | 102.77 ± 0.08 | 99.39 ± 0.43 |
| 7 | 100.59 ± 0.19 | 98.54 ± 0.71 | 92.01 ± 1.27 |
| 14 | 101.63 ± 0.19 | 99.56 ± 0.72 | 92.96 ± 1.28 |
| 21 | 99.25 ± 1.41 | 95.98 ± 1.50 | 84.54 ± 1.34 |
| 30 | 98.50 ± 1.64 | 95.17 ± 0.07 | 82.88 ± 4.35 |
| 60 | 98.52 ± 0.02 | 91.51 ± 1.17 | 70.25 ± 4.27 |
| 90 | 94.04 ± 4.28 | 86.36 ± 0.90 | 56.00 ± 11.70 |
| 120 | 92.79 ± 1.01 | 79.02 ± 1.05 | 53.43 ± 6.30 |
| 150 | 90.18 ± 3.14 | 77.42 ± 0.71 | 40.37 ± 14.41 |
| 180 | 85.56 ± 4.58 | 72.32 ± 0.38 | 37.10 ± 12.35 |

TABLE 2

Changes in amount of potassium salt in water for injection (WFI) (mean ± standard deviation)

Potassium salt in WFI

| | Residual amount (%) | | |
|---|---|---|---|
| Time (day) | 25° C. | 40° C. | 60° C. |
| 0 | 106.71 ± 0.29 | 106.71 ± 0.29 | 106.71 ± 0.29 |
| 3 | 107.86 ± 0.58 | 107.73 ± 3.13 | 104.29 ± 0.50 |
| 7 | 103.92 ± 1.20 | 105.87 ± 2.04 | 101.76 ± 0.09 |
| 14 | 106.28 ± 1.29 | 104.97 ± 0.47 | 100.81 ± 0.83 |
| 21 | 98.94 ± 0.99 | 96.58 ± 0.38 | 90.02 ± 2.81 |
| 30 | 98.55 ± 0.43 | 95.66 ± 0.24 | 90.09 ± 1.88 |
| 60 | 97.73 ± 1.02 | 93.24 ± 3.04 | 87.38 ± 1.55 |

TABLE 2-continued

Changes in amount of potassium salt in water for injection (WFI) (mean ± standard deviation)

Potassium salt in WFI

| | Residual amount (%) | | |
|---|---|---|---|
| Time (day) | 25° C. | 40° C. | 60° C. |
| 90 | 97.41 ± 0.02 | 92.91 ± 1.11 | 87.25 ± 1.55 |
| 120 | 97.40 ± 0.53 | 92.84 ± 0.91 | 86.37 ± 1.43 |
| 150 | 96.88 ± 3.09 | 91.72 ± 0.92 | 86.62 ± 0.83 |
| 180 | 95.99 ± 0.56 | 90.59 ± 0.83 | 84.68 ± 2.02 |

TABLE 3

Changes in amount of lithium salt in water for injection (WFI) (mean ± standard deviation)

Lithium salt in WFI

| | Residual amount (%) | | |
|---|---|---|---|
| Time (day) | 25° C. | 40° C. | 60° C. |
| 0 | 99.67 ± 0.12 | 99.67 ± 0.12 | 99.67 ± 0.12 |
| 3 | 99.72 ± 0.30 | 99.42 ± 0.22 | 99.28 ± 1.02 |
| 7 | 99.63 ± 0.35 | 98.33 ± 1.14 | 95.34 ± 1.02 |
| 14 | 98.91 ± 0.41 | 97.21 ± 0.41 | 94.78 ± 2.58 |
| 21 | 98.81 ± 1.67 | 95.05 ± 0.40 | 94.47 ± 2.18 |
| 30 | 95.51 ± 0.52 | 90.89 ± 1.00 | 93.40 ± 0.61 |
| 60 | 93.40 ± 0.81 | 89.61 ± 1.31 | 83.11 ± 0.47 |
| 90 | 90.40 ± 0.68 | 88.80 ± 0.24 | 81.84 ± 0.62 |
| 120 | 90.34 ± 0.58 | 88.07 ± 0.48 | 81.53 ± 2.36 |
| 150 | 89.73 ± 2.47 | 87.65 ± 3.22 | 80.81 ± 2.08 |
| 180 | 87.81 ± 1.51 | 84.63 ± 2.90 | 75.59 ± 3.15 |

As shown in the above Tables, the amount of each salt tended to decrease gradually with the passage of time, and as temperature increased, more amounts decreased.

In particular, the stability profile of potassium-salt compound was better than that of sodium- and lithium-salt compound.

Experimental Example 2

Stability Test of Oral Preparation

The powder of each salt (sodium salt, potassium salt, lithium salt), as prepared in Example 4-6, was filled into a vial and allowed stored in vacuo. It was then stored at different temperatures (25° C., 40° C., 60° C.) for 6 months and the amount of active ingredients in powder were measured by HPLC.

The following Tables 4, 5 and 6 show the remaining amount of active ingredients in powder per period.

TABLE 4

Changes in amount of sodium salt in powder form (mean ± standard deviation)

Sodium salt (solid)

| | Residual amount (%) | | |
|---|---|---|---|
| Time (day) | 25° C. | 40° C. | 60° C. |
| 0 | 101.33 ± 1.02 | 101.33 ± 1.02 | 101.33 ± 1.02 |
| 3 | — | — | — |

TABLE 4-continued

Changes in amount of sodium salt in powder
form (mean ± standard deviation)

Sodium salt (solid)

Residual amount (%)

| Time (day) | 25° C. | 40° C. | 60° C. |
|---|---|---|---|
| 7 | 100.75 ± 6.24 | 100.81 ± 3.35 | 101.27 ± 4.45 |
| 14 | 100.45 ± 1.24 | 100.69 ± 0.29 | 101.14 ± 0.50 |
| 21 | 99.76 ± 0.70 | 100.57 ± 0.48 | 100.15 ± 1.14 |
| 30 | 99.61 ± 3.21 | 100.46 ± 0.27 | 100.10 ± 0.75 |
| 60 | 99.60 ± 0.16 | 100.07 ± 0.16 | 99.91 ± 1.18 |
| 90 | — | — | — |
| 120 | 99.51 ± 1.70 | 99.94 ± 1.15 | 99.81 ± 2.28 |
| 150 | — | — | — |
| 180 | 99.19 ± 2.28 | 99.89 ± 1.11 | 99.75 ± 0.20 |

TABLE 5

Changes in amount of potassium salt in powder
form (mean ± standard deviation)

Potassium salt (solid)

Residual amount (%)

| Time (day) | 25° C. | 40° C. | 60° C. |
|---|---|---|---|
| 0 | 100.43 ± 0.30 | 100.43 ± 0.30 | 100.43 ± 0.30 |
| 3 | — | — | — |
| 7 | — | — | — |
| 14 | — | — | — |
| 21 | — | — | — |
| 30 | 100.31 ± 0.25 | 100.28 ± 1.10 | 99.60 ± 0.50 |
| 60 | 100.20 ± 0.55 | 100.14 ± 0.80 | 99.56 ± 0.85 |
| 90 | 100.17 ± 0.46 | 100.10 ± 0.71 | 99.27 ± 0.80 |
| 120 | 100.07 ± 0.43 | 99.81 ± 0.78 | 99.03 ± 0.90 |
| 150 | — | — | — |
| 180 | 100.03 ± 0.80 | 99.78 ± 0.31 | 98.87 ± 0.92 |

TABLE 6

Changes in amount of lithium salt in powder
form (mean ± standard deviation)

Lithium salt (solid)

Residual amount (%)

| Time (day) | 25° C. | 40° C. | 60° C. |
|---|---|---|---|
| 0 | 98.56 ± 0.89 | 98.56 ± 0.89 | 98.56 ± 0.89 |
| 3 | — | — | — |
| 7 | 98.32 ± 0.32 | 98.16 ± 0.09 | 97.49 ± 0.80 |
| 14 | 97.69 ± 2.58 | 96.18 ± 3.28 | 96.45 ± 2.80 |
| 21 | 96.87 ± 1.64 | 96.02 ± 2.49 | 95.87 ± 2.09 |
| 30 | 95.01 ± 1.10 | 95.96 ± 0.89 | 95.69 ± 2.97 |
| 60 | 94.78 ± 8.09 | 95.70 ± 6.88 | 95.51 ± 1.99 |
| 90 | — | — | — |
| 120 | 92.69 ± 1.03 | 95.58 ± 1.38 | 94.84 ± 0.56 |
| 150 | — | — | — |
| 180 | 90.85 ± 1.61 | 95.40 ± 2.37 | 92.48 ± 3.14 |

As shown in the above Tables 4, 5 and 6, the stability profile of samples in powder form was better than those in solution. The changes in the amount of each powder sample at 25° C. were not observed.

Therefore, the test results show that the potassium- and sodium-salt compounds in powder form were relatively stable in high temperatures; ensuring an increased stability profile as oral preparation.

Experimental Example 3

Acute Toxicity Test of Free-base Dosage Form in Rats

The specific pathogen-free SD (Sprague Dawley) male rats, 6-8 weeks of age, were employed for this experiment. After the compounds were dissolved in physiological saline, the sample was administered intravenously in the tail vein of the animals using a disposable syringe. Each sample was administered at a single dose. 14 days after administration, mortalities were recorded for the different dose levels, as shown in Tables 7-9.

TABLE 7

Acute toxicity test results of free base form in rats

| Dose (mg/kg) | Number of dead animals/Number of drug-treated animals | Estimated $LD_{50}$ values |
|---|---|---|
| 52 | 0/7 | 115~150 mg/kg |
| 68 | 1/7 | |
| 89 | 3/7 | |
| 115 | 3/7 | |
| 150 | 6/7 | |
| 171 | 6/7 | |
| 184 | 7/7 | |
| 195 | 7/7 | |

TABLE 8

Acute toxicity test results of potassium salt in rats

| Dose (mg/kg) | Number of dead animals/Number of drug-treated animals | Estimated $LD_{50}$ dose |
|---|---|---|
| 50 | 0/6 | 200~250 mg/kg |
| 100 | 0/6 | |
| 150 | 0/6 | |
| 200 | 0/6 | |
| 250 | 3/3 | |
| 300 | 1/1 | |
| 500 | 2/2 | |

TABLE 9

Acute toxicity test results of sodium salt in rats

| Dose (mg/kg) | Number of dead animals/Number of drug-treated animals | Estimated $LD_{50}$ dose |
|---|---|---|
| 50 | 0/5 | 225~250 mg/kg |
| 100 | 0/5 | |
| 150 | 0/7 | |
| 175 | 1/7 | |
| 200 | 2/7 | |
| 225 | 2/7 | |
| 250 | 5/5 | |

As noted Tables 7-9, the salt forms of potassium and sodium has less toxicity than free base. Thus demonstrating that these salt forms of the invention played a role to significantly improve the toxicity profile of the desired compound itself.

Experimental Example 4

Protective Effects of Tetrafluorobenzyl-5-aminosalicylic Acid Compound and Its Salts in Rats with Focal Cerebral Ischemia by Occluding Middle Cerebral Artery Using each compound produced in Example 3-5, the protective effects of tetrafluorobenzyl-5-aminosalicylic acid compound represented by chemical formula I, together with its potassium and sodium salts were examined in rats with focal cerebral ischemia by occluding middle cerebral artery.

The specific pathogen-free SD (Sprague Dawley) male rats were subject to focal cerebral ischemia by occlusion of the middle cerebral artery for 60 minutes and treated with drugs after reperfusion. Animals were euthanized 24 hours later and brains removed. Infarct volume was analyzed after staining brain slices with triphenyltetrazolium chloride (TTC), as shown in FIG. 1.

As noted in FIG. 1, the three compounds showed similar protection against focal cerebral ischemia.

The invention claimed is:

1. A process for preparing tetrafluorobenzyl-5-aminosalicylic acid derivative represented by Chemical Formula I and its pharmaceutically acceptable salt, the process is comprised of the following steps:
   a) oxidation of tetrafluorobenzyl alcohol, represented by Chemical Formula 1, to tetrafluorobenzaldehyde, represented by Chemical Formula 2;
   b) conversion of tetrafluorobenzaldehyde to tetrafluorobenzilidine-5-aminosalicylic acid derivative, represented by Chemical Formula II, via dehydration-condensation reaction between tetrafluorobenzaldehyde and 5-amino-salicylic acid, represented by Chemical Formula 3, and
   c) hydrogenation of tetrafluorobenzilidine-5-aminosalicylic acid derivative to tetrafluorobenzyl-5-aminosalicylic acid derivative, represented by Chemical Formula I <Chemical formula I>

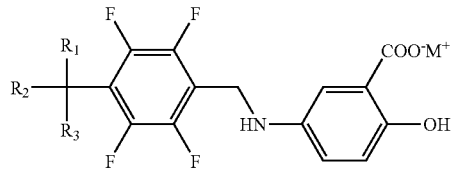

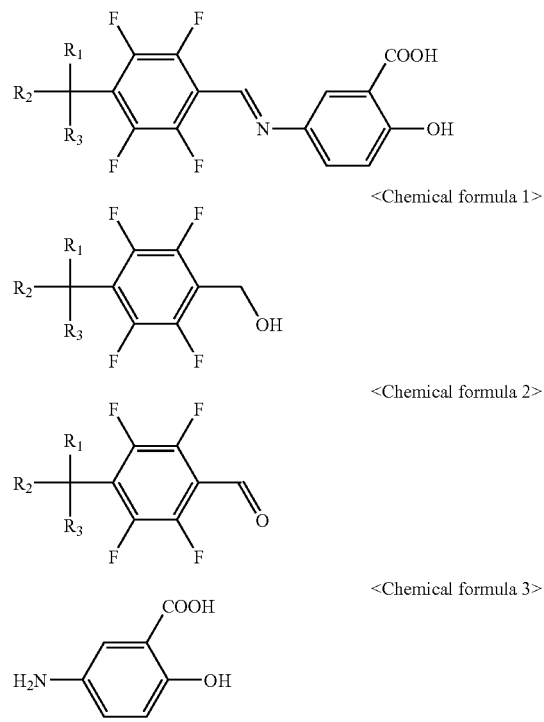

Wherein, $M^+$ represents lithium, sodium or potassium; and $R_1$, $R_2$ and $R_3$ may, independently of one another, be hydrogen or halogen.

2. The process according to claim 1, wherein tetrafluorobenzaldehyde and 5-amino-salicylic acid undergo a dehydration-condensation reaction in the presence of methylene chloride solvent at room temperature using molecular sieves to form tetrafluorobenzilidine-5-aminosalicylic acid derivative, represented by Chemical Formula II.

3. The process according to claim 1, wherein tetrafluorobenzilidine-5-aminosalicylic acid derivative is hydrogenated to reduce the imine group and the salts of tetrafluorobenzyl-5-aminosalicylic acid derivative can be prepared by direct crystallization or lyophilization using an inorganic reagent selected from the group consisting of lithium hydroxide, sodium hydroxide and potassium hydroxide in the presence of alcohol, acetone, or acetonitrile.

* * * * *